United States Patent
Golinski et al.

(10) Patent No.: US 6,528,045 B1
(45) Date of Patent: Mar. 4, 2003

(54) PROCESS FOR THE PREPARATION OF STABLE AQUEOUS HAIR DYEING EMULSIONS

(75) Inventors: Frank Golinski, Darmstadt (DE); Heribert Lorenz, Gross-Bieberau (DE)

(73) Assignee: Goldwell GmbH (DE)

( * ) Notice: Subject to any disclaimer, the term of this patent is extended or adjusted under 35 U.S.C. 154(b) by 0 days.

(21) Appl. No.: 09/406,028

(22) Filed: Sep. 27, 1999

(30) Foreign Application Priority Data

Oct. 14, 1998 (DE) ......................................... 198 47 224

(51) Int. Cl.$^7$ .................................................. A61K 7/13
(52) U.S. Cl. ..................... 424/70.1; 424/70.6; 424/401; 8/404; 8/405; 8/406
(58) Field of Search ............................... 424/70.6, 70.1, 424/401; 8/404, 405, 406

(56) References Cited

U.S. PATENT DOCUMENTS 5,525,123 A * 6/1996 Lorenz et al. ................. 8/408
5,817,155 A * 10/1998 Yasuda et al. ................. 8/406

* cited by examiner

*Primary Examiner*—Shelley A. Dodson
*Assistant Examiner*—Konata M. George
(74) *Attorney, Agent, or Firm*—Norris, McLaughlin & Marcus P.A.

(57) ABSTRACT

A stable, aqueous hair dyeing emulsion with good Theological properties is prepared, while simultaneously substantially reducing the manufacturing time and energy consumption, comprising at least one oxidation hair dyestuff precursor, by mixing a water-in-oil emulsion, comprising 10% to 50% by weight of at least one nonionic emulsifier, 10% to 50% by weight of at least one nonionic co-emulsifier selected from the group of $C_{10}$–$C_{22}$-fatty alcohols, $C_{12}$–$C_{18}$-fatty acid mono- and dialkanolamides and/or $C_{10}$–$C_{22}$-fatty acid esters with polyvalent alcohols, 5% to 40% by weight of oleic acid, and up to 25%, in particular 20% by weight of water, each calculated to the total w/o-emulsion composition, with an aqueous phase comprising at least one water-soluble surfactant. Mixing is carried out under shear force at 15° to 30° C., preferably at room temperature at about 20° to 25°.

6 Claims, No Drawings

PROCESS FOR THE PREPARATION OF STABLE AQUEOUS HAIR DYEING EMULSIONS

BACKGROUND OF THE INVENTION

The present invention concerns an improved process for the preparation of stable, aqueous hair dyeing emulsions.

Compositions for the permanent dyeing of human hair, customarily comprising an oxidation dyestuff precursor, namely a developing-coupling system, are customarily used in the form of aqueous emulsions (see K. Schrader, "Grundlagen und Rezepturen der Kosmetika", 2nd. Ed. (1989), pp. 797 ff.).

Their preparation is carried out by hot emulsification of the components and subsequent cooling, which naturally needs energy and time, and does not always lead to stable emulsions.

There was therefore a need to optimize the currently applied manufacturing process.

DETAILED DESCRIPTION OF THE INVENTION

It has now been found that a stable, aqueous hair dyeing emulsion comprising at least one oxidation hair dyestuff precursor with good rheological properties can be obtained, while simultaneously substantially reducing the manufacturing time and respective energy consumption, by mixing a water-in-oil emulsion, comprising 10% to 50% by weight, of at least one nonionic emulsifier, 10% to 50% by weight of at least one nonionic co-emulsifier selected from the group $C_{10}$–$C_{22}$-fatty alcohols. $C_{12}$–$C_{18}$-fatty acid mono- and -dialkanolamides and/or $C_{10}$–$C_{22}$-fatty acid esters with polyvalent alcohols, 5% to 40% by weight of oleic acid and up to 25%, in particular 20% by weight of water, each calculated to the total w/o-emulsion composition, with an aqueous phase comprising at least one water-soluble surfactant. Mixing is carried out under shear force at 15° to 30° C., preferably at room temperature at about 20 to 25° C.

The final product thus achieved preferably has a viscosity between 5,000 and 30,000, in particular 7,500 and 25,000, especially preferred about 10,000 to 20,000 mPa·s, measured at 20° C. in a Brookfield Viscosimeter RVT.

The proportion of the oil phase in the total emulsion preferably is between about 5% to about 40%, preferably 10% to 30% by weight, calculated to the total emulsion.

The water-in-oil emulsion may also contain about 0% to 20% by weight of an oil.

Preferred oily components in the oil phase are customary cosmetic oils and fats, for example, natural oils such as avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, or olive oil, soya oil, lanolin and the derivatives thereof, as well as mineral oils such as paraffin oil and petrolatum. Synthetic oils and waxes are, for example, silicone oils, polyethylene glycols, etc. Further suitable hydrophobic components are in particular fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, polyethyleneglycol and polyglyceryl fatty acid esters such as PEG-7-glyceryl cocoate, etc.

Suitable nonionic emulsifiers are in particular the various $C_{10}$–$C_{22}$-fatty alcohol ethoxylates, such as lauryl, myristyl, cetyl, oleyl, tridecyl, isotridecyl, coco fatty and tallow fatty alcohol ethoxylates, etc.; however, further nonionic oil-soluble emulsifiers known per se may also be used. The average number of ethylenexide molecules per molecule of fatty alcohols is between about 2 and 15, preferably about 4 to 10.

Further suitable nonionic emulsifiers are $C_8$–$C_{18}$-alkyl polyglucosides with a condensation degree of preferably 1.1 to 3, in particular 1.2 to 2.5, which have been known per se for some time. Also suited for this purpose are further nonionic surfactants, for example amineoxides such as lauryl dimethyl amineoxide, e.g. of the type "Ammonyx$^R$", "Aromax$^R$" or "Genaminox$^R$".

Suitable nonionic emulsifiers for w/o-emulsions, the quantity of which preferably ranges between about 15% to 40%, in particular about 20% to 35% by weight, calculated to the w/o-emulsion, are principally known as state of the art, for example, from the standard monography of K. Schrader, "Grundlagen und Rezepturen der Kosmetika", 2nd Ed., pp. 387–525 (1989).

The co-emulsifier, used according to the invention in amounts from 10% to 50%, preferably about 15% to 45%, in particular about 20% to 40% by weight, calculated to the w/o emulsion, and also exerting a thickening and consistency-regulating effect, is selected from the group of $C_8$–$C_{22}$-fatty alcohols, $C_{12}$–$C_{18}$-fatty acid monoalkanolamides and/or $C_{10}$–$C_{22}$-fatty acid esters of polyvalent alcohols. Of these fatty alcohols, especially preferred are coco fatty alcohol, lauryl alcohol, decyl alcohol, tridecyl alcohol, myristyl alcohol, cetyl alcohol, stearyl alcohol and mixtures thereof. Preferred $C_{12}$–$C_{18}$-fatty acid alkanolamides are Cocamide MEA, Cocamide DEA, Cocamide MIPA, Lauramide MEA, Lauramide DEA, Oleamide MEA, Oleamide DEA, Stearamide MEA, Stearamide DEA and Stearamide MIPA. Suitable $C_{10}$–$C_{22}$-fatty acid esters of polyvalent alcohols are in particular the ethyleneglycol, propyleneglycol, polyethyleneglycol, glycerol and sorbitan esters of lauric acid, coco fatty acid, myristic acid or stearic acid and mixed esters thereof, such as, for example, polyethyieneglycol (PEG-)-glyceryl fatty acid esters. These components are also known and described in Schrader, l.c.

As essential component, the w/o emulsion finally comprises oleic acid, preferably in an amount from 5% to 40%, preferably about 10% to 30%, in particular about 15% to 25% by weight, calculated to the total emulsion.

An additional preferred component in the w/o emulsions is oleyl alcohol, preferably in an amount from about 5% to 15% by weight, either as additional component or also as fatty alcohol-component of the co-emulsifier. This component particularly improves the aesthetic appearance of the final emulsion.

The water content in the water-in-oil emulsion is at most 20% by weight thereof.

The w/o emulsion is preferably prepared by melting the fatty-phase components at about 50° to 80° C., addition of water and cooling down to about 15° to 30° C. while stirring intensively.

Water-soluble surfactants used in the water phase and incorporated into the final product by mixing the w/o emulsion with the water phase to prepare the oil-in-water emulsion are anionic, arnphoteric or zwitterionic and/or cationic, as well as, optionally, specific nonionic surfactants. These are present in amounts from about 0.25% to about 5% by weight, preferably about 0.4% to 2.5% by weight, calculated to the total composition of the ready-to-use oil-in-water emulsion.

Suitable anionic surfactants are those of the sulfate, sulfonate, carboxylate and alkyl phosphate type, especially, of course, those customarily used in hair treatment compositions, in particular, the known $C_{10}$–$C_{18}$-alkyl sulfates, and the respective ether sulfates, for example, $C_{12}$–$C_{14}$-alkyl ether sulfate, lauryl ether sulfate, especially with 1 to 4 ethylene oxide groups in the molecule, acyl aminocarboxylic acids, such as lauroyl sarcosinate and glutamate, furthermore monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and alkali salts of sulfosuccinic acid semiesters, for example, the disodium salt of monooctyl sulfosuccinate and alkali salts of long-chain monoalkyl ethoxy sulfosuccinates. Suitable surfactants of the carboxylate type are alkyl polyether carboxylic acids and the salts thereof of the formula

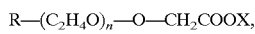

wherein R is a $C_8$–$C_{20}$-alkyl group, preferably a $C_{12}$–$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

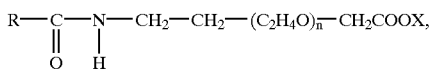

wherein R and X have the above meanings, and n stands in particular for a number from 1 to 10, preferably 2.5 to 5.

Such products have been known for some time and are on the market, for example, under the trade name "AKYPO®" and "AKYPO-SOFT®".

Also useful are $C_8$–$C_{20}$-acyl isethionates, alone or in admixture with other surfactants, and sulfofatty acids and the esters thereof.

It is also possible to use amphoteric or zwitterionic surfactants as water-soluble emulsifiers, in particular also in admixture with anionic surfactants.

Useful as such are the various known betaines such as fatty acid arnidoalkyl betaines and sulfobetaines, for example, lauryl hydroxy sulfobetaine; long-chain alkyl amino acids, such as cocoaminoacetate, cocoaminopropionate and sodium cocoamphopropionate and -acetate have also proven suitable.

In detail, it is possible to use betaines of the structure

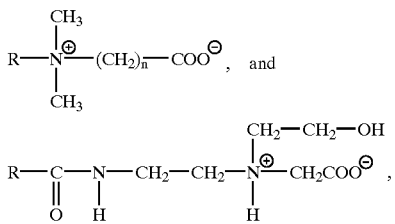

wherein R is a $C_8$–$C_{18}$-alkyl group and n is 1 to 3; sulfobetaines of the structure

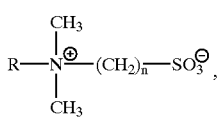

wherein R is a $C_8$–$C_{18}$-alkyl group and n is 1 to 3;

and amidoalkyl betaines of the structure and amidoalkyl betaines of the structure

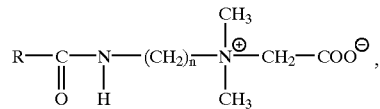

wherein R is a $C_8$–$C_{18}$-alkyl group and n is 1 to 3.

Also useful in small quantities are nonionic, water-soluble surfactants, for example, $C_8$–$C_{18}$-alkyl polyglucosides with a polymerization degree of 1 to 5, in particular in admixture with anionic and/or amphoteric or zwitterionic surface-active substances.

Further useful surfactants are cationic surfactants, such as the known quaternary ammonium compounds with one or two alkyl or alkenyl groups with 10 to 22 carbon atoms in the molecule, in particular in an amount from 0.1% to 5%, preferably 0.25% to 5%, especially preferred 0.5% to 2.5% by weight, calculated to the total composition, alone or preferably in admixture with amphoteric or zwitterionic, or optionally, nonionic surfactants.

Suitable long-chain quaternary ammonium compounds which can be used alone or in admixture are in particular cetyl trimethyl ammonium chloride, dimethyl dicetyl ammonium chloride, trimethyl cetyl ammonium bromide, behenyl trimonium chloride, stearyl trimethyl ammonium chloride, hydroxyethyl hydroxycetyl dimonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, lauryl trimethyl ammonium chloride, tris-(oligooxyethyl) alkyl ammonium phosphate, cetyl pyridinium chloride, cetyl pyridinium chloride, etc. Basically suitable are all quaternary ammonium compounds listed under the generic name "Quaternium" in the CTFA International Cosmetic Ingredient Dictionary.

The hair dyeing emulsion prepared according to the invention comprises at least one oxidation dyestuff precursor; useful is a mixture of at least one developing and at least one coupling agent.

These are known per se and described, for example, in the monography of K. Schrader, "Grundlagen und Rezepturen der Kosmetika", 2nd Ed. (1989), pp. 784–799.

Examples of developing substances are in particular 1,4-diaminobenzene, 2,5-diaminotoluene, tetraaminopyrimidines, triaminohydroxypyrimidines, 1,2,4-triaminobenzene, 2-(2,5-diamino-phenyl)ethanol, 2-(2'-hydroxyethyl amino)-5-arninotoluene and 1-amino-4-bis-(2'-hydroxy-ethyl)-aminobenzene, or the water-soluble salts thereof; examples for coupling substances are resorcinol, 2-methyl resorcinol, 4-chlororesorcinol, 2-amino-4-chlorophenol, 4-(N-methyl)aminophenol, 2-aminophenol, 3-aminophenol, 1-methyl-2-hydroxy-4-aminobenzene, 3-N, N-dimethyl aminophenol, 4-amino-3-methyl phenol, 5-amino-2-methyl phenol, 6-amino-3-methyl phenol, 3-amino-2-methyl amino-6-methoxypyridine, 2-amino-3-hydroxypyridine, 4-aminodiphenylamine, 4,4'-diaminodiphenylamine, 2-dimethyl amino-5-aminopyridine, 2,6-diaminopyridine, 1,3-diaminobenzene, 1-amino-3-(2'-hydroxyethyl amino)benzene, 1-amino-3-[bis(2'-hydroxyethyl) amino]benzene, 1,3-diaminotoluene, α-naphthol, 1,4-diamino-2-chlorobenzene, 4,6-dichlororesorcinol, 4-hydroxy-1,2-methylene dioxybenzene, 1,5-di-hydroxynaphthaline, 1,7-dihydroxynaphthaline, 2,7-dihydroxy-naphthaline, 1-hydroxy-naphthaline, 4-hydroxy-1,2-methylene dioxybenzene, 2,4-diamino-3-chlorophenol, and/or 1-methoxy-2-amino-4-(2'-hydroxyethyl amino) benzene, whereby this list is just exemplary.

Developing and coupling substances are preferably contained in a molar proportion of 1:3 to 5:1, in particular about 1:1 and about 3:1; their proportion in the hair dyeing emulsions prepared according to the invention may range from about 0.1% to about 5% by weight, depending on the desired coloration.

It is useful to incorporate these oxidation dyestuff precursors already into the aqueous phase, however, if desired, they can also be added together with the oil phase or subsequently thereto.

Optionally, the compositions prepared according to the invention can also comprise so-called shading agents for the fine-tuning of the desired shade, in particular also direct-acting dyestuffs.

Such shading agents are, for example, nitro dyestuffs, such as 2-amino-4,6-dinitrophenol, 2-amino-4-nitrophenol, 2-amino-6-chloro-4-nitrophenol, etc., preferably in amounts from about 0.05% to 2.5%, in particular 0.1% to 1% by weight, calculated to the dyeing composition (excluding the oxidation composition).

Preparation of the final oil-in-water emulsion is carried out by stirring the water-in-oil emulsion into the aqueous phase at about 15° to 30° C., in particular at room temperature, i.e. at about 20° to 25° C., at about 5,000 to 15,000, in particular 8,000 to 12,000 r/pm.

The hair dyeing composition emulsions according to the invention can comprise the basic substances and additives customarily found in such compositions, conditioning agents, stabilizers, thickening agents, complexing agents, etc., known as state of the art and described, for example, in the monography of K. Schrader, "Grundlagen und Rezepturen der Kosmetika", 2nd Ed. (Huthig Buch Veriag, Heidelberg, 1989), pp. 782 to 815.

The hair dyeing emulsions prepared according to the invention preferably have a pH-value in the alkaline range, in particular between about 8 and about 12.5, preferably between 8.5 and 11, adjusted in particular by the addition of ammnonia.

The viscosity of the ready-to-use oil-in-water emulsion preferably ranges between about 5,000 to 30,000, in particular about 7,500 to 25,000, especially preferred from about 10,000 to 20,000 mPa·s, measured at 20° C. in a Brookfield Viscosimeter RVT.

For application, the oxidation dyestuff precursor emulsion is mixed with an oxidation agent composition. The preferred oxidation agent is hydrogen peroxide, for example, in concentrations between 2% to 6%.

However, it is also possible to use other peroxides, such as urea peroxide and melamine peroxide.

The pH-value of the ready-to-use hair dyeing composition, i.e. after admixture with peroxide, may be in the slightly acidic range, i.e. between 5.5 to 6.9, in the neutral range and in the alkaline range, i.e. between pH 7.1 and 10.

Following are two Examples to illustrate the invention.

By mixing the fatty-phase components at about 60° C. and subsequent addition of water with intensive stirring, then cooling to about 25° C., the following water-in-oil emulsions were prepared:

| Compositions | No. 1 | No. 2 | No. 3 | No. 4 |
|---|---|---|---|---|
| Cetearyl alcohol | 32 | — | — | 32 |
| Stearic acid monoethanolamide | — | 32 | — | — |
| Ethanediol distearate | — | — | 32 | — |
| Oleic acid | 16 | 16 | 16 | 16 |
| Oleth-5 | 32 | 22 | 32 | — |
| Oleyl alcohol | 10 | 10 | 10 | 10 |
| Laureth-12 | — | 10 | — | — |
| Lauryl polyglucoside (P.D. ~1.5) | — | — | — | 22 |
| Water ad | 100 | 100 | 100 | 100% by wt. |

30% by weight of each of the water-in-oil emulsions Nos. 1, 2, 3 or 4 were stirred at 9,000 r/pm at 20° to 25° C. into two different aqueous surfactant compositions:

| Composition | No. I | No. II |
|---|---|---|
| W/O emulsions according to examples 1, 2, 3 or 4 | 30 | 30 |
| Hydroxycetyl hydroxyethyl dimonium chloride | 0.5 | — |
| Sodium lauryl sulfate | — | 0.5 |
| Ammonia ad pH | 8.5 | 10.5 |
| Water ad | 100.0 | 100.0% by wt. |

Viscosity: About 15,000 to 20,000 mPa·s, measured in a Brookfield Viscosimeter RVT at 20° C.

The emulsions thus obtained show stability during storage and, upon addition of aqueous oxidation dyestuff precursor compositions, which may optionally contain further additives, can be packed as hair dyeing emulsions mixable with peroxides.

What is claimed is:

1. Process for the preparation of stable, aqueous hair dyeing emulsions, comprising at least one oxidation dyestuff precursor, whereby a water-in-oil emulsion (A), comprising
   a) 10% to 50% by weight, of at least one nonionic emulsifier,
   b) 10% to 50% by weight, of at least one nonionic co-emulsifier selected from the group of $C_{10}$–$C_{22}$-fatty alcohols, $C_{12}$–$C_{18}$-fatty acid mono-and dialkanolamides, and $C_{10}$–$C_{22}$-fatty acid esters with polyvalent alcohols,
   c) 5% to 40% by weight of oleic acid, and
   d) up to 25% of water, each calculated to the total water-in-oil emulsion composition, is mixed with an aqueous phase (B), comprising at least one water-soluble surfactant, under shear force at 15° to 30° C.

2. Process according to claim 1, wherein the oxidation dyestuff precursor is added to the oil-in-water emulsion obtained after admixture of the water-in-oil emulsion (A) with the aqueous phase (B).

3. Process according to claim 1, wherein the water-in-oil emulsion (A) comprises about 5%. to 15% by weight, calculated to the composition thereof, of oleyl alcohol.

4. Process according to claim 1, wherein the oil-in-water emulsion obtained by admixture of the water-in-oil emulsion (A) with the aqueous phase (B), has a pH-value of about 8 and about 12.5.

5. Process according to claim 1, wherein the oil-in-water emulsion obtained by admixture of the water-in-oil emulsion (A) with the aqueous phase (B) has a viscosity of about 5,000 to 30,000 mPa·s, measured in a Brookfield Viscosimeter RVT at 20° C.

6. Emulsion for the dyeing of human hair, prepared according to claim 1.

* * * * *